United States Patent
Schara et al.

(10) Patent No.: US 6,648,817 B2
(45) Date of Patent: Nov. 18, 2003

(54) APPARATUS AND METHOD FOR STEREO VIEWING IN VARIABLE DIRECTION-OF-VIEW ENDOSCOPY

(75) Inventors: Nathan J. Schara, Pasadena, CA (US); Hans D. Høeg, Arcadia, CA (US); Eric L. Hale, South Pasadena, CA (US)

(73) Assignee: EndActive, Inc., Arcadia, CA (US)

( * ) Notice: Subject to any disclaimer, the term of this patent is extended or adjusted under 35 U.S.C. 154(b) by 64 days.

(21) Appl. No.: 10/002,468

(22) Filed: Nov. 15, 2001

(65) Prior Publication Data

US 2003/0092966 A1 May 15, 2003

(51) Int. Cl.[7] .................................................. A61B 1/00
(52) U.S. Cl. ....................................... 600/173; 600/166
(58) Field of Search ................................. 600/173, 111, 600/166, 176, 129, 109; 348/65, 82–85; 359/367; 356/241

(56) References Cited

U.S. PATENT DOCUMENTS

| | | | |
|---|---|---|---|
| 3,880,148 A | | 4/1975 | Kanehira |
| 3,918,438 A | * | 11/1975 | Hayamizu et al. .......... 600/168 |
| 4,697,577 A | | 10/1987 | Forkner |
| 4,895,431 A | * | 1/1990 | Tsujiuchi et al. ............. 359/29 |
| 4,926,257 A | * | 5/1990 | Miyazaki ...................... 348/45 |
| 5,166,787 A | * | 11/1992 | Irion ............................ 348/75 |
| 5,222,477 A | * | 6/1993 | Lia .............................. 600/111 |
| 5,494,483 A | * | 2/1996 | Adair ........................... 600/111 |
| 5,577,991 A | * | 11/1996 | Akui et al. ................... 600/111 |
| 5,762,603 A | | 6/1998 | Thompson |
| 6,309,345 B1 | * | 10/2001 | Stelzer et al. ................ 600/106 |
| 6,371,909 B1 | * | 4/2002 | Hoeg et al. .................. 600/173 |

FOREIGN PATENT DOCUMENTS

| | | |
|---|---|---|
| WO | WO 99/42028 | 8/1999 |
| WO | WO 01/22865 | 4/2001 |

\* cited by examiner

*Primary Examiner*—John P. Leubecker
(74) *Attorney, Agent, or Firm*—Morrison & Foerster

(57) ABSTRACT

A variable direction-of-view endoscope (74) with a spherical viewing window (34) symmetric about a symmetry plane (52) sealed to a distal end portion (18). The endoscope optical system can be adjusted to vary the direction of a view vector (22) through an unlimited range (50) about a pivot axis (23). The spherical viewing window (34) enables a process that switches the device between an initial configuration (54) and a final configuration (56), both having the same viewing direction (55). In addition to providing the user with an alternative to a possibly unfavorable viewpoint, this redundancy enables a stereo imaging process which captures (66) and displays (72) a stereo image pair (70) affording the user three-dimensional viewing.

24 Claims, 11 Drawing Sheets

Prior Art

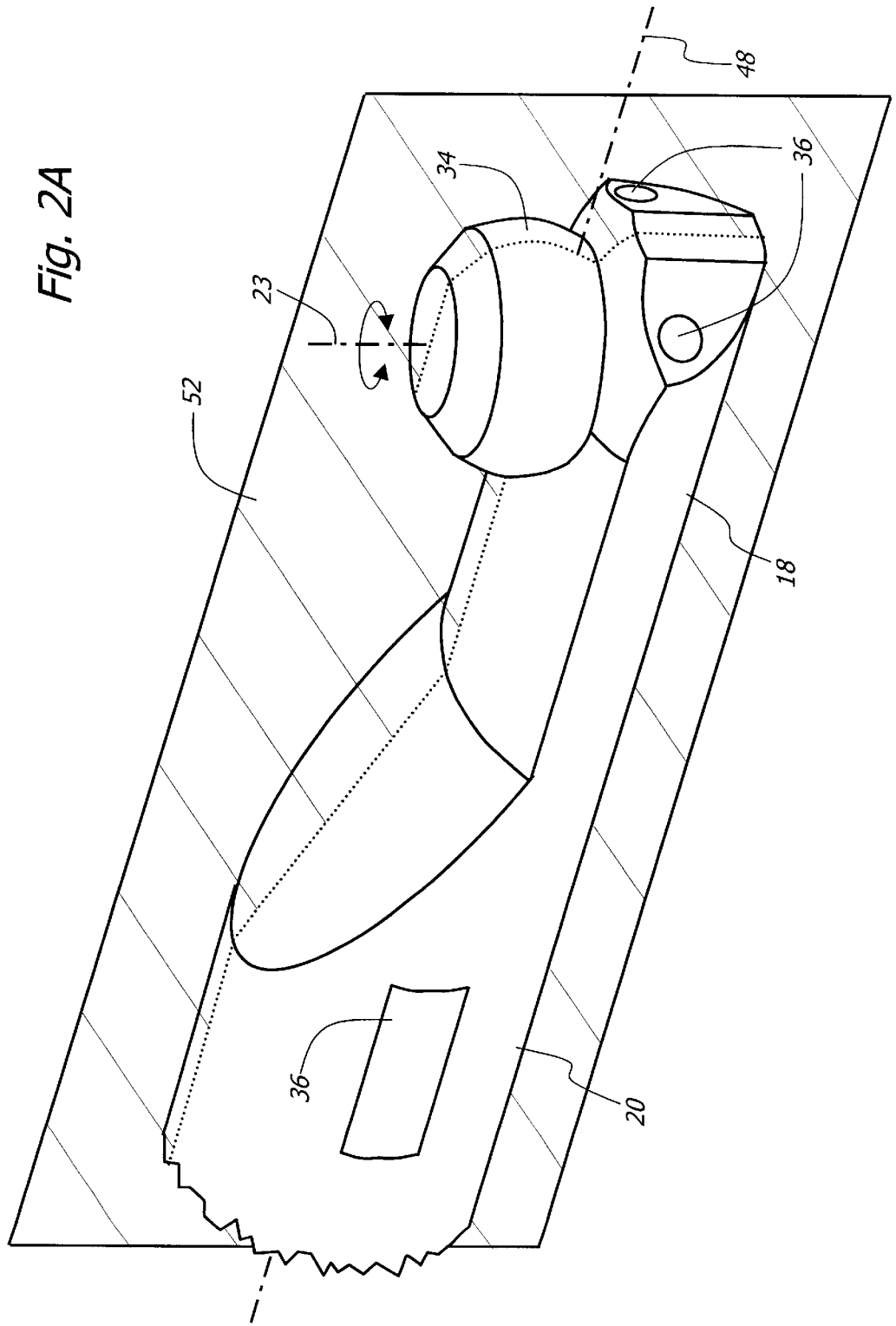

APPARATUS AND METHOD FOR STEREO VIEWING IN VARIABLE DIRECTION-OF-VIEW ENDOSCOPY

FIELD OF THE INVENTION

The present invention relates to endoscopes (including devices such as borescopes, fiberscopes, etc.) and specifically to variable direction-of-view and stereo viewing endoscopic devices.

BACKGROUND OF THE INVENTION

Endoscopes are elongated devices used to visualize the inside of cavities. They are commonly utilized for medical and industrial applications. There has been a long felt need for endoscopes capable of varying their direction-of-view.

Most rigid endoscopes capable of varying their direction of view have a window that limits their scanning range. U.S. Pat. No. 4,697,577 to Forkner (1987) discloses a swing prism type of endoscope with a direction-of-view variable between 30 and 70 degrees from forward. WIPO publication WO 01/22865 by Ramsbottom (2001) discloses a similar device for varying the direction of view between 0 and 120 degrees. These two examples demonstrate an additional shortcoming of existing swing prism endoscopes: they only view on one side of the shaft axis. Other types of variable direction-of-view endoscopes, such as that disclosed in U.S. Pat. No. 5,762,603 to Thompson, have similar limitations.

An apparatus intended to solve these problems was disclosed in WIPO publication WO 99/42028 by Hoeg et al. (1999). This endoscope features a retractable rotatable housing that can protrude beyond the outer diameter of the endoscope shaft. The housing has a window that moves with the viewing direction. This design is unnecessarily complex and has potential sealing, electrical, and mechanical problems. Consequently this design has never been implemented, and therefore all the variable direction-of-view endoscopes heretofore known suffer from a number of disadvantages, including:

a) A generally limited direction-of-view range, which restricts viewing freedom and does not allow the user to look directly backwards, a feature that would be useful in many situations.

b) A limited view of the region directly in front of the endoscope, making it difficult to investigate the targeted area due to the user being unable view alternate sides of the shaft axis without rotating the endoscope.

c) Only one unique viewpoint for each particular view due to the fact that there are no redundant viewing configurations, resulting in the user having no alternative to an unfavorable viewpoint.

d) Difficult interpretation of depth in the view, as existing variable direction-of-view endoscopes do not provide a way to accomplish three-dimensional viewing.

From the discussion above, it should become apparent that there is a need for a variable direction-of-view endoscope that will provide an increased or unlimited scanning range which gives the user increased viewing freedom and backwards viewing capability; provide a swing-through-center capability by centering the direction of view range on the forward direction; provide redundant viewing capability such that each particular view direction can be obtained from multiple unique viewpoints; and provide the user with three-dimensional imaging to ease the interpretation of depth in the view.

BRIEF SUMMARY OF THE INVENTION

In accordance with the present invention, a variable direction-of-view endoscope comprises an adjustable imaging system and a symmetric viewing window. The imaging system includes a pivotable optical component. The device features redundant viewing configurations that can be switched between using a simple flipping process. Additional steps to provide the user with three-dimensional viewing are also disclosed. The term "endoscope" as used herein is defined as an endoscope used for medical procedures, a borescope, a fiberscope, etc.

What is claimed is an apparatus for use as an endoscope, comprising a generally tubular member having a distal end portion, a proximal end portion, and a longitudinal axis; a viewing system, comprising a pivotable view vector originating from said distal end portion, wherein said pivotable view vector has a pivot axis that is not parallel to either said pivotable view vector or said longitudinal axis; a viewing window attached to said distal end portion, wherein said viewing window comprises a transparent viewing area about a symmetry plane, wherein said symmetry plane is generally parallel to both said pivot axis and said longitudinal axis near said distal end portion, and wherein said pivotable view vector passes through said transparent viewing area; a means for controllably rotating said distal end portion about said longitudinal axis; and a means for controllably rotating said pivotable view vector about said pivot axis.

BRIEF DESCRIPTION OF THE DRAWINGS

FIG. 2A is a perspective view of the distal end of an endoscope according to the preferred embodiment of the invention.

DETAILED DESCRIPTION OF THE INVENTION

The following detailed description illustrates the invention by way of example, not by way of limitation of the principles of the invention. This description will clearly enable one skilled in the art to make and use the invention, and describes several embodiments, adaptations, variations, alternatives and uses of the invention, including what we presently believe is the best mode of carrying out the invention.

Prior Art Devices

Figure 1A:
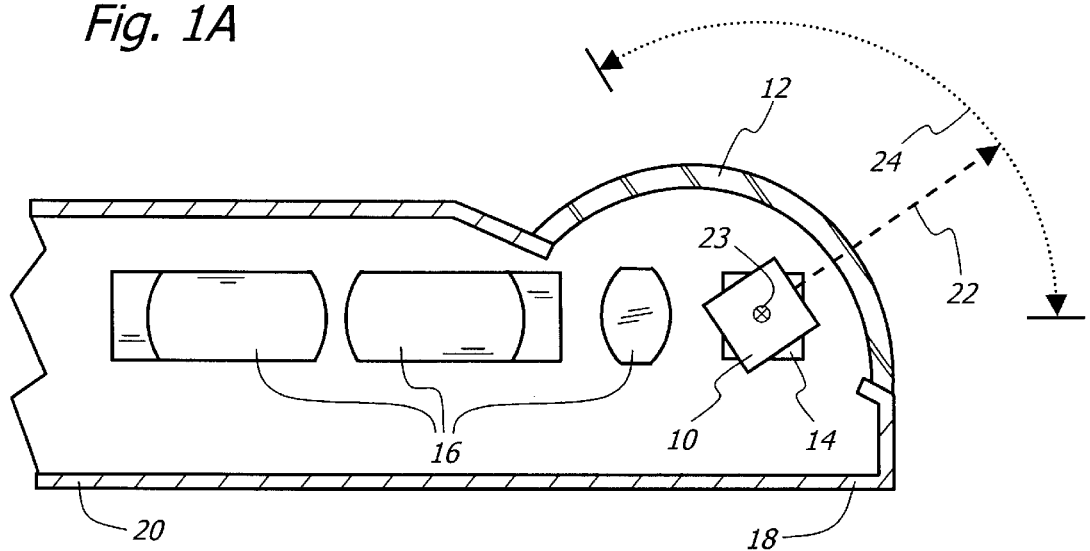
FIGS. 1A, 1B, and 1C show examples of the prior art.
Figure 1B:
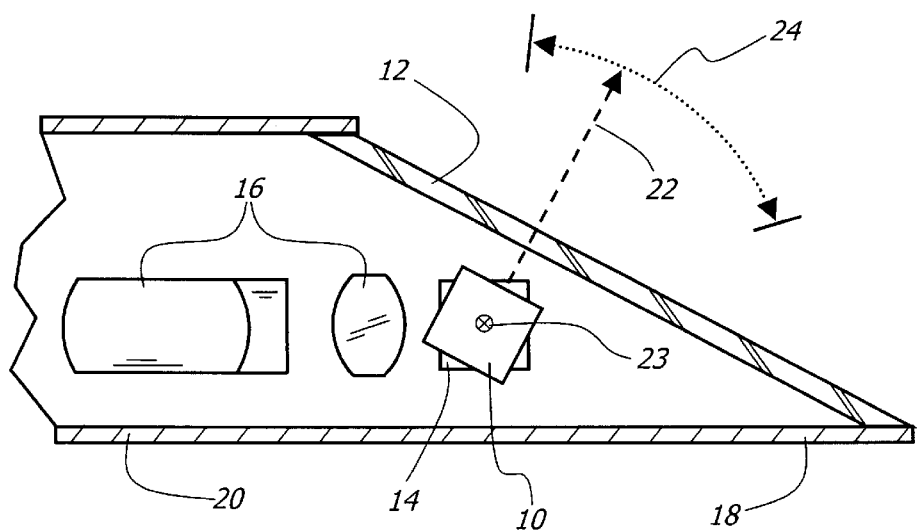

Referring now to the drawings, in which like reference numbers represent similar or identical structures throughout, FIGS. 1A and 1B are schematic sectional views of the distal end of traditional variable direction-of-view swing prism endoscopes. A pivotable reflector 10, usually a prism, reflects light received through a viewing window 12 to a fixed reflector 14, also a prism, which further reflects the light into an optical train 16 for transmission to the viewer (not shown). These optical elements are mounted in the distal end portion 18 of a tubular member 20. The view vector 22 is adjusted by rotating the pivotable reflector 10 about the pivot axis 23. Each of these designs has a limited range 24 over which the view vector 22 can be varied.

Figure 1C:
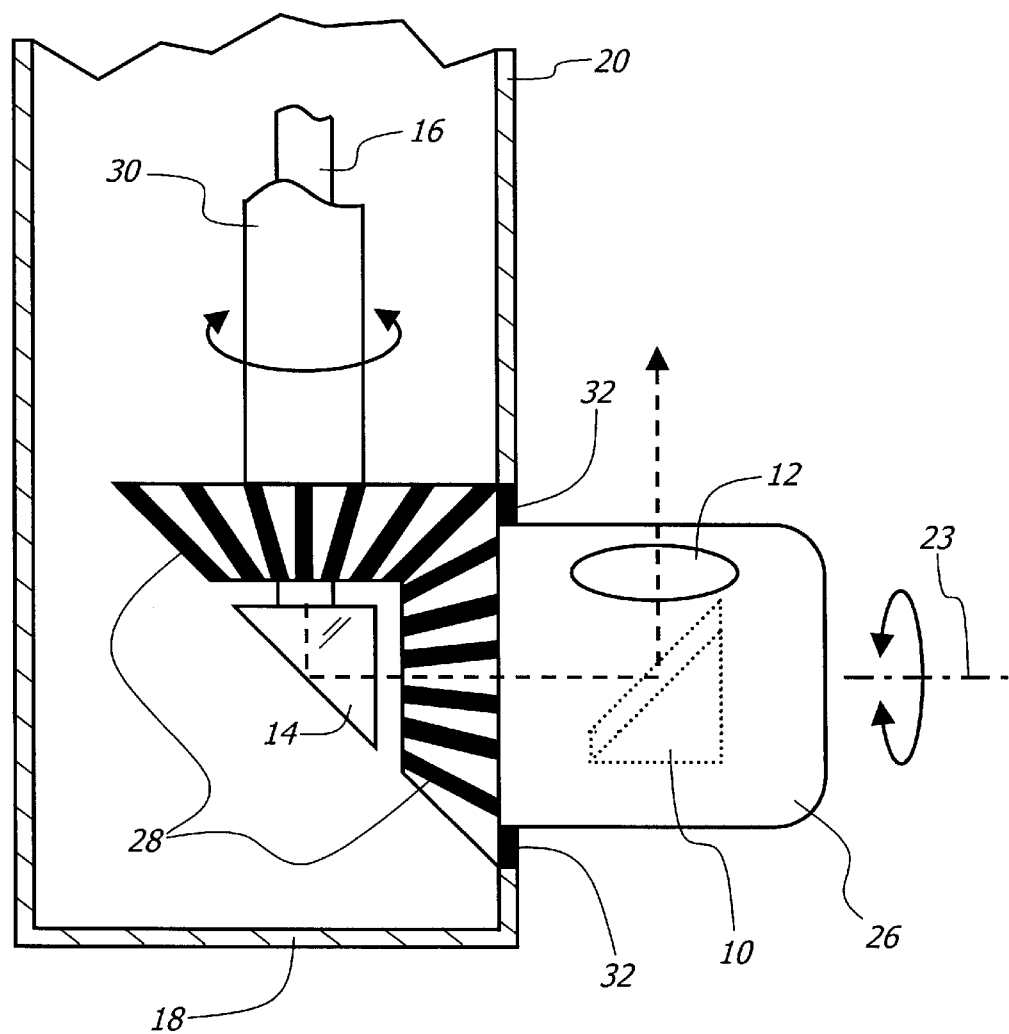

In another example of prior art shown in FIG. 1C, a pivotable reflector 10 is mounted in a rotatable housing 26. The light enters through a viewing window 12, is reflected to a fixed reflector 14 and then into an optical train 16. The housing 26 is pivoted about the pivot axis 23 using a pair of gears 28 and a drive shaft 30. The interface 32 between the rotatable housing 26 and the distal end portion 18 of the tubular member 20 is difficult to seal and poses significant threats of leakage and contamination.

Preferred Embodiment

A preferred embodiment of the distal end of an endoscope according to the present invention is shown in FIG. 2A. A rigid metal distal end portion 18 is disposed at the distal end of a tubular member 20. It should be appreciated that the tubular member 20 may be constructed as either rigid or flexible to suit the particular application. A generally spherical viewing window 34 is sealed to the distal end portion 18. The window 34 comprises a transparent layer of rigid material, such as glass, that seals the endoscope against fluids and other debris. Of course, alternate materials for window 34 that accomplish the same sealing and viewing goals are also possible. The overall size of the distal end portion 18 is reduced near the window 34 to permit rearward viewing. Illumination is delivered through illumination ports 36 on the front and sides of the distal end portion 18 using standard light guides or optical fibers (not shown).

Figure 2B:
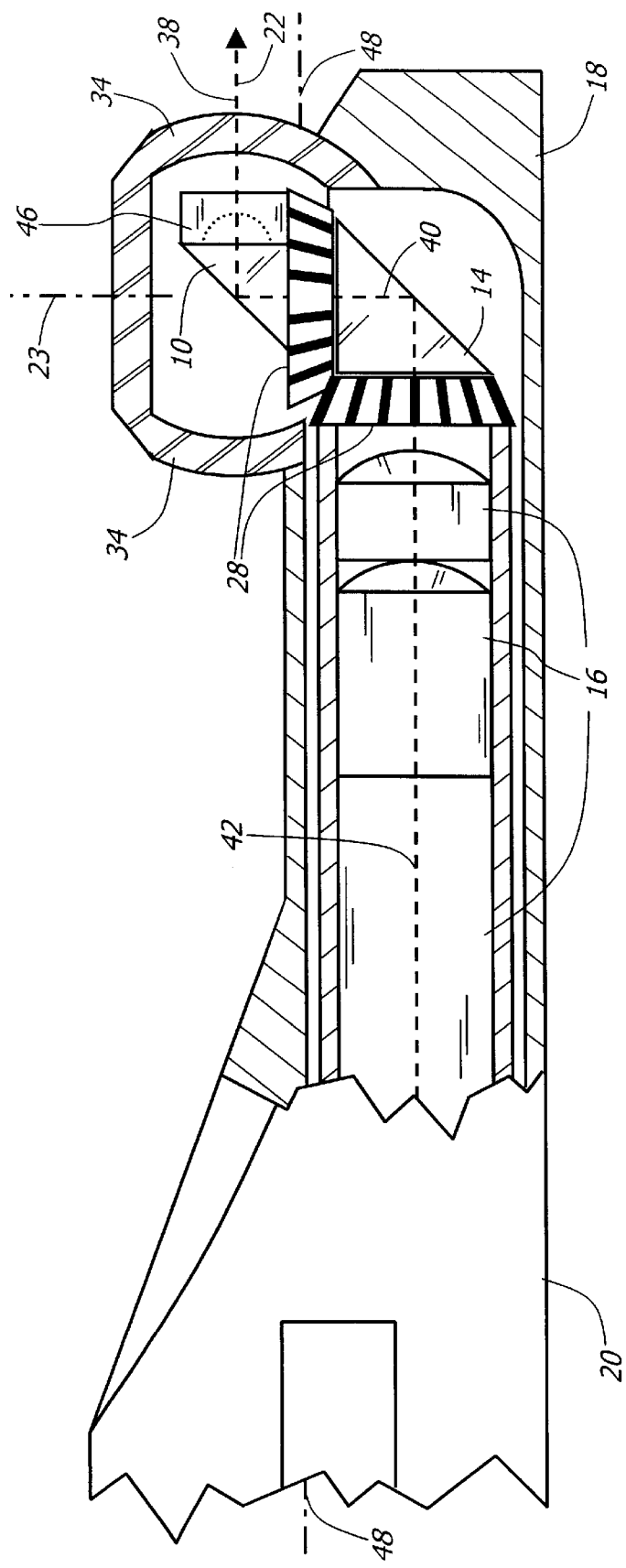
FIG. 2B is a side view of the distal end depicted in FIG. 2A according to the preferred embodiment of the invention.

FIG. 2B shows a partial section side view of the preferred embodiment of the present invention. A pivotable reflector 10 is positioned inside the spherical viewing window 34 and a fixed reflector 14 is positioned adjacent to the pivotable reflector 10 in the reduced distal end portion 18. An optical train 16 formed by a series of lenses is disposed inside the tubular member 20 between the fixed reflector 14 and a viewer (not shown), such as a camera. A pair of metal gears 28 is used to control the rotation of the pivotable reflector 10 about the pivot axis 23. Alternative actuation means such as pull-wires or push-rods may also be acceptable depending on the particular application.

In the preferred embodiment, the pivotable reflector 10 and fixed reflector 14 are both glass prisms. However, it should be appreciated that the pivotable reflector 10 and fixed reflector could be made of other materials, such as plastic, or may be a mirrored surface based on any rigid material. It should also be appreciated that the reflectors 10, 14 do not have to be the same and could be any combination of reflector types, such as the ones mentioned above.

The pivotable reflector 10 and the fixed reflector 14 are positioned in the distal end portion 18 so as to define an optical path comprising three segments 38, 40, 42. This path passes from a viewed scene outside the endoscope (not shown), through the spherical viewing window 34, to the pivotal reflector 10, to the fixed reflector 14, and then along the optical train 16 to the viewer (not shown). The first optical path segment 38 passes from the viewed scene (not shown) through the spherical viewing window 34 to the pivotable reflector 10. The second optical path segment 40 passes from the pivotable reflector 10 to the fixed reflector 14, coincident with the pivot axis 23. The third optical path segment 42 passes from the fixed reflector 14 along the optical train 16 to the viewer (not shown). Additional lenses such as a negative objective 46 are positioned along the optical path to facilitate image transmission and improve optical performance. It should be noted that the first optical path segment 38 is offset from the longitudinal axis 48 of the endoscope. A view vector 22 exists in coincidence with the first optical path segment 38.

Figure 2C:
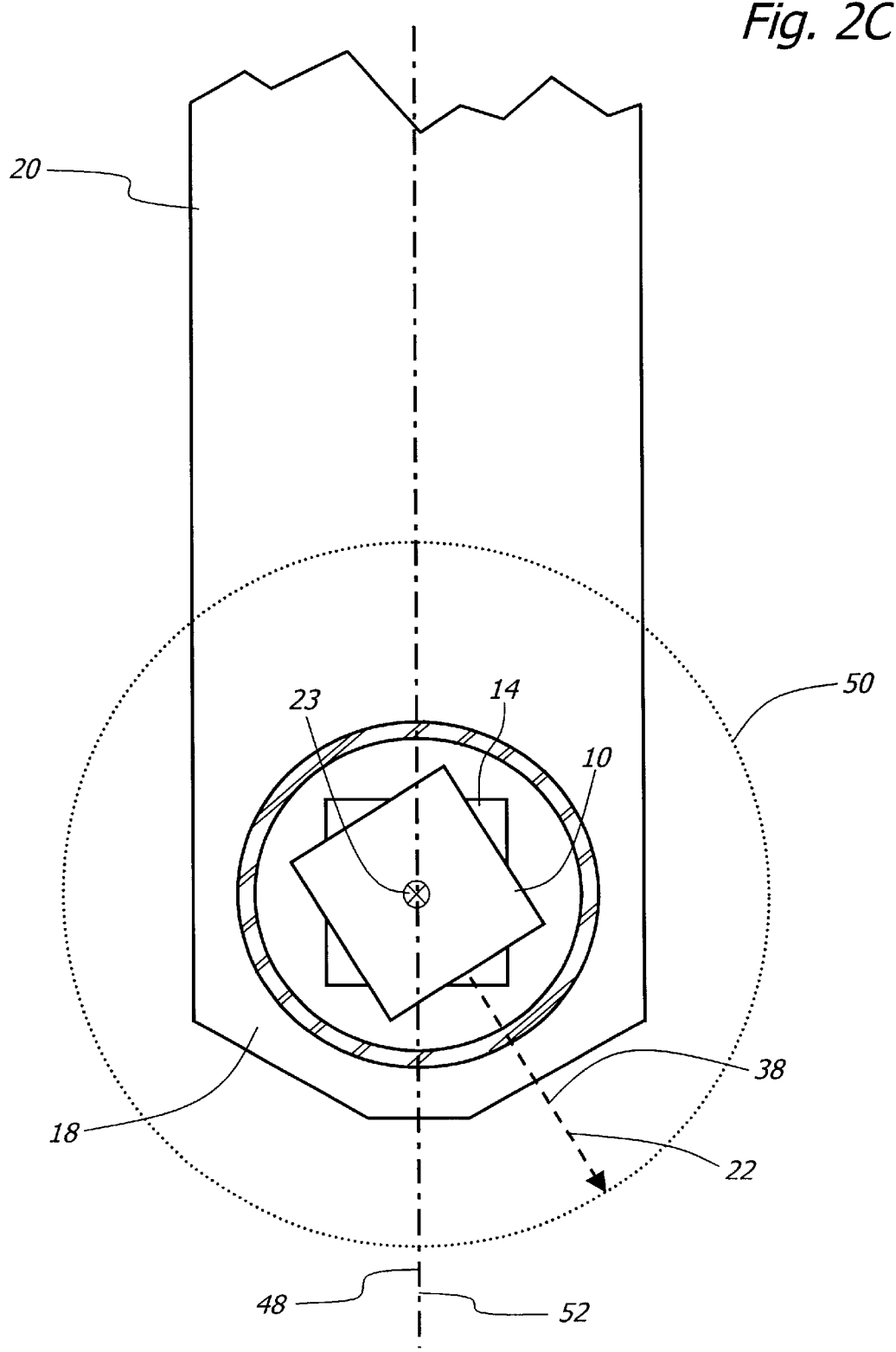
FIG. 2C is a top view of the distal end depicted in FIG. 2A according to the preferred embodiment of the invention.

By rotating the pivotable reflector 10, the first optical path segment 38 and view vector 22 may be swept through an unlimited range 50, as shown in FIG. 2C. This unlimited range 50 includes portions on either side of a symmetry plane 52, which is parallel to the longitudinal axis 48 and the pivot axis 23. The pair of gears 28 allows this unlimited rotation to be controlled from the proximal end of the endoscope (not shown). The view vector 22 may be swept about the longitudinal axis 48 by pivoting the distal end portion 18 about the longitudinal axis 48 through rotation of the shaft 20.

Figure 3:
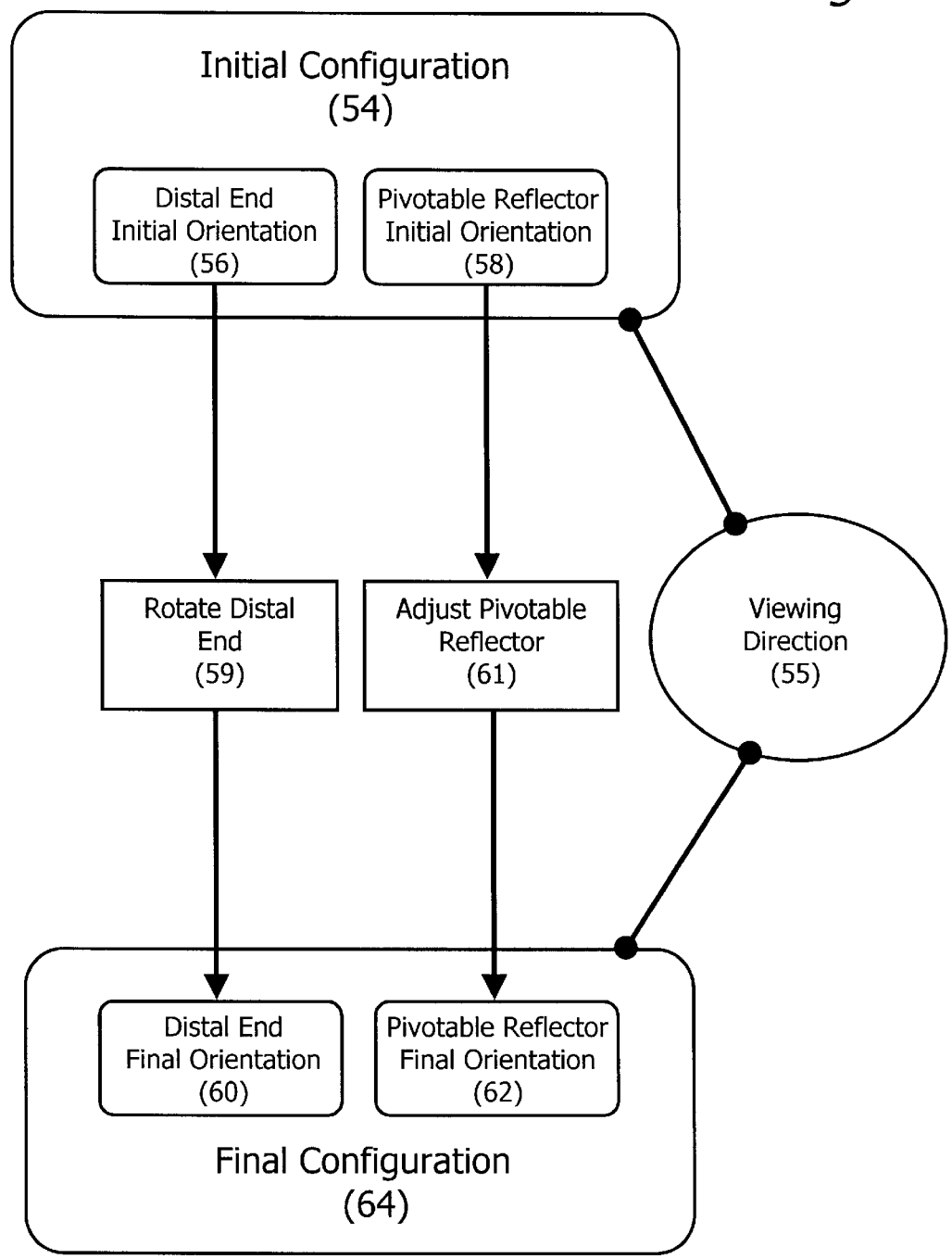
FIG. 3 is a flow chart illustrating a redundant configuration flipping process according to the preferred embodiment of the invention.
Figure 4A:
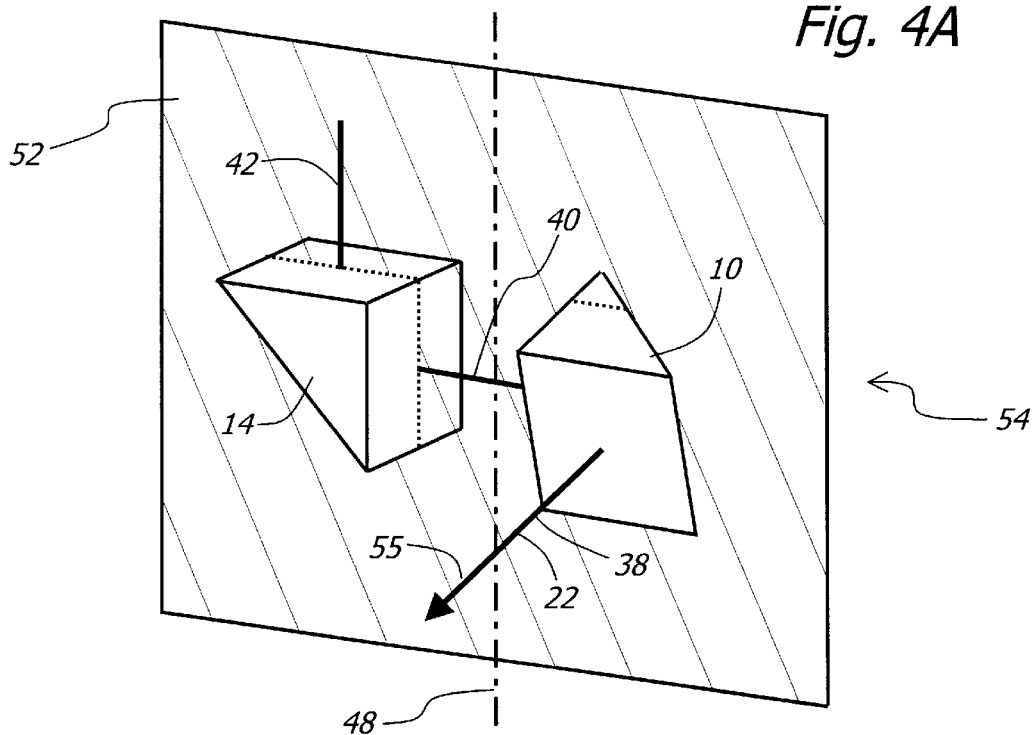
FIGS. 4A and 4B show initial and final configurations of the redundant configuration flipping process illustrated in FIG. 3.
Figure 4B:
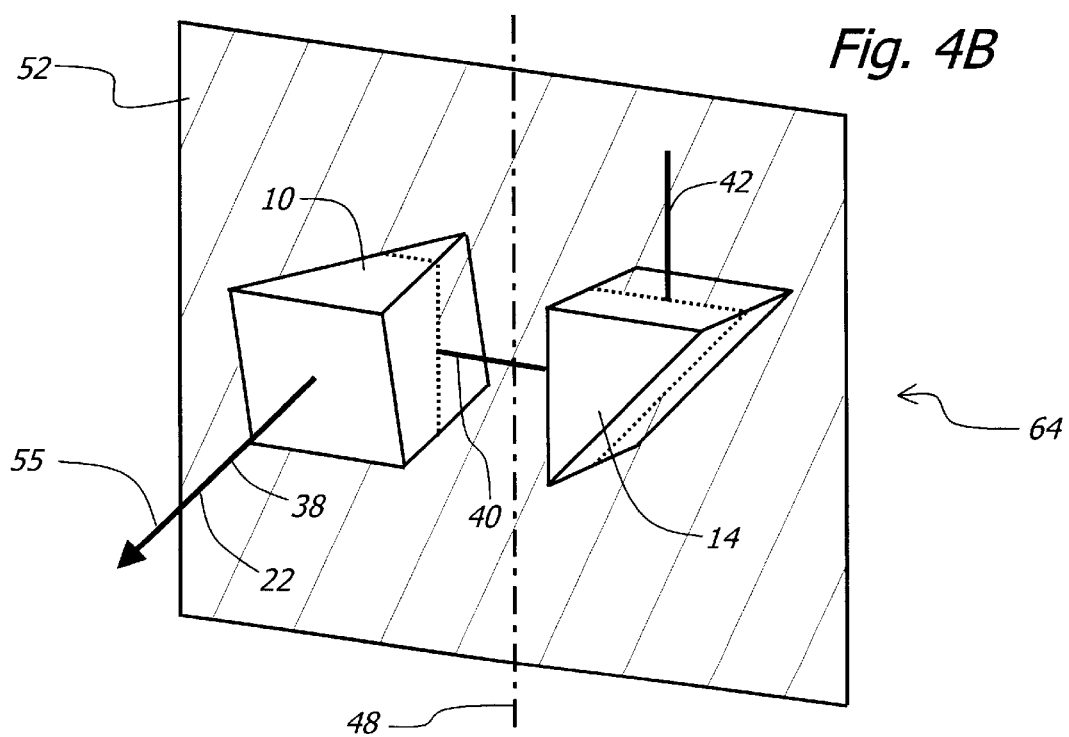

FIGS. 3, 4A and 4B illustrate a process of operating the endoscope of the preferred embodiment of the present invention to view in the same direction from two separate view points. This process adjusts the endoscope without causing a net change in the direction of the view vector 22. At the outset, the endoscope has an initial configuration 54, having a certain viewing direction 55. The two reflectors 10, 14 and the three optical path segments 38, 40, 42 shown in FIG. 4A represent this initial endoscope configuration 54. The initial endoscope configuration 54 can be any arbitrary configuration comprising an initial distal end orientation 56 and an initial pivotable reflector orientation 58.

The process of adjusting the endoscope involves primarily two steps. In the first step 59, the distal end portion is rotated by approximately 180 degrees about the longitudinal axis 48 from the initial distal end orientation 56 to a final distal end orientation 60. This causes the pivotable reflector 10 and the fixed reflector 14 to be rotated about the longitudinal axis 48 by 180 degrees. In the second step 61 the pivotable reflector 10 is adjusted to a final pivotable reflector orientation 62 that is symmetric across the symmetry plane 52 from the initial pivotable reflector orientation 58. These two steps can be executed in any order or simultaneously. A final endoscope configuration 64 comprising a final distal end orientation 60 and a final pivotable reflector orientation 62 is thus achieved. The two reflectors 10, 14 and the three optical path segments 38, 40, 42 shown in FIG. 4B represent this final endoscope configuration 64.

The final endoscope configuration 64 has the same viewing direction 55 as the initial endoscope configuration 54 but is mirrored, or flipped, across the longitudinal axis 48. It should be noted that the view vector 22 in the final configuration shown in FIG. 4B is offset from the view vector 22 in the initial configuration shown in FIG. 4A. Consequently, this redundant configuration flipping process can be used to view in the same direction from two different configurations of the endoscope.

Figure 5:
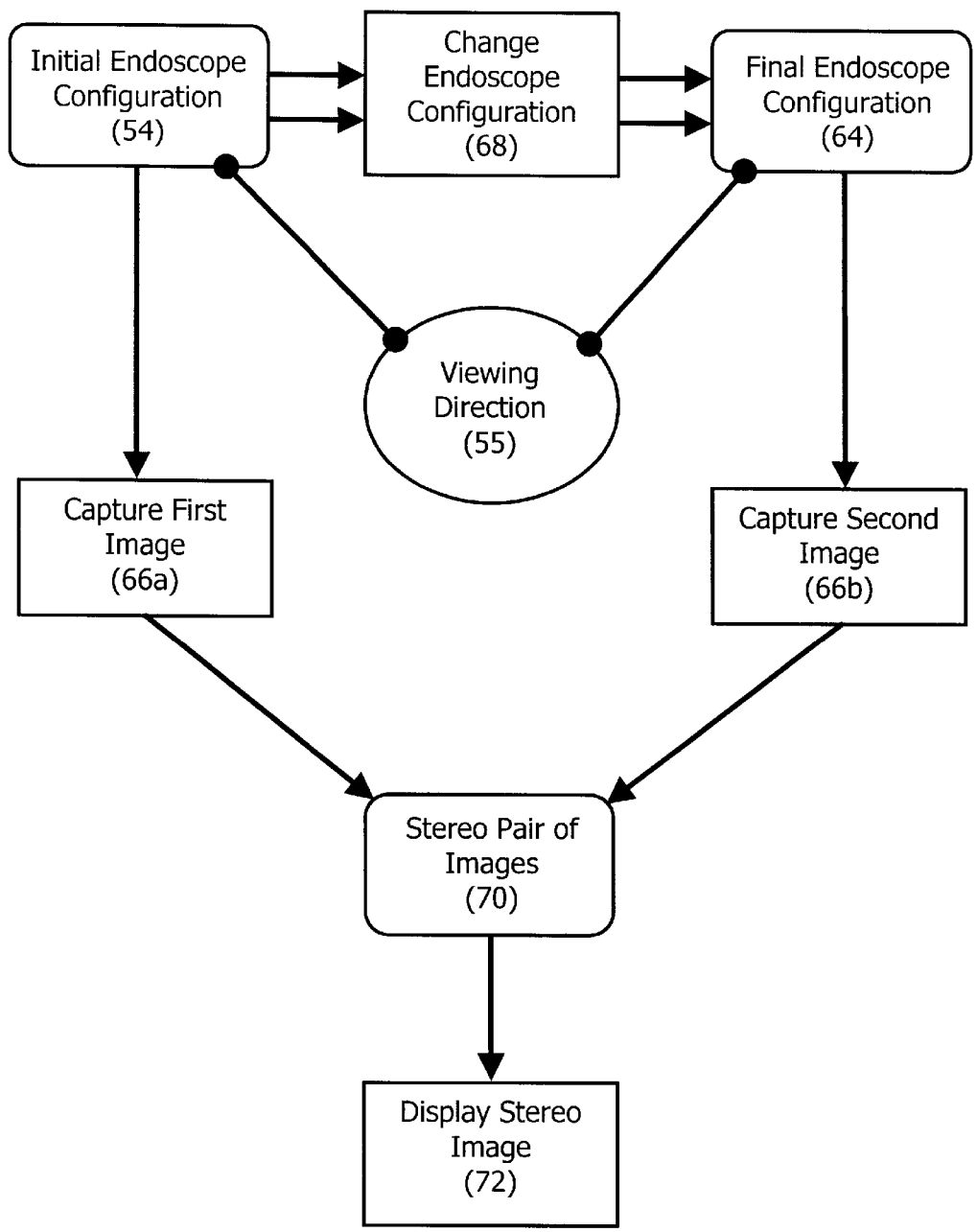
FIG. 5 is a flow chart illustrating a stereo imaging process according to the preferred embodiment of the invention.

The redundant configuration flipping process is a part of a four-step process used to provide three-dimensional viewing with the endoscope of the preferred embodiment. FIG. 5 illustrates this stereo imaging process. In the first step 66a, a first image is captured from an initial endoscope configuration 54, having a viewing direction 55. In the second step 68, the view vector is offset by changing the endoscope configuration to a final endoscope configuration 64 with the same viewing direction 55. When using the endoscope of the present embodiment, this second step 68 is accomplished by the redundant configuration flipping process described above. Other endoscopes may require a different process to reach the final configuration 64. In the third step 66b, a second image is captured from the final endoscope configuration 64. The two captured images constitute a stereo pair of images 70. In the fourth step 72, the stereo pair 70 is displayed using a stereo image display device. This could be any standard stereo image display device such as a stereo viewing headset or a monitor with alternately displayed frames coupled with synchronized LCD shutter glasses.

Figure 6:
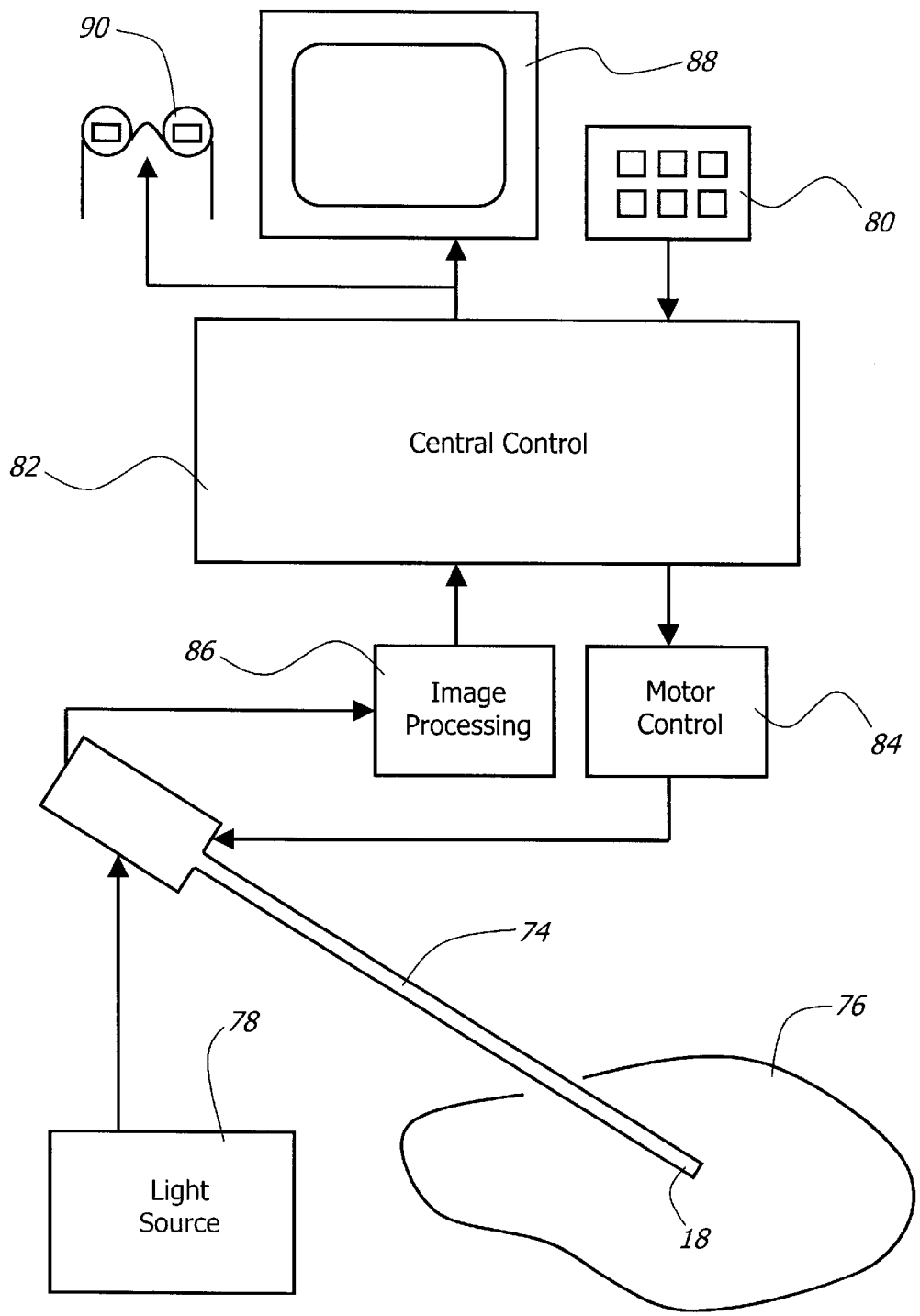
FIG. 6 is a schematic of a complete system according to the preferred embodiment of the invention.

FIG. 6 illustrates a complete system according to a preferred embodiment of the present invention. An endoscope 74 according to the present invention is positioned with its distal end portion 18 in a cavity 76. Illumination is delivered to the endoscope 74 from a light source 78. The operator controls the system through a keypad 80 or other appropriate input device. This input is received by a central control unit 82, which in turn directs a motor control unit 84. The motor control unit 84 controls the configuration of the endoscope 74 through actuators in the endoscope 74. An image processing unit 86 receives image signals from the endoscope 74 and adjusts the signals as needed. The central control unit 84 receives the adjusted signals from the image processing unit 86 and relays the signals to a video display device 88 and a stereo image display device 90. The central control unit 82, the motor control unit 84, and the image processing unit 86 may be implemented as a personal computer running an appropriate control program. They may alternatively be constructed as dedicated hardware devices.

This complete system is set up to accomplish the stereo imaging process described above. As part of this system the motor control unit 84 and the endoscope 74 are together configured to effect the redundant configuration flipping process described above.

Figure 7A:
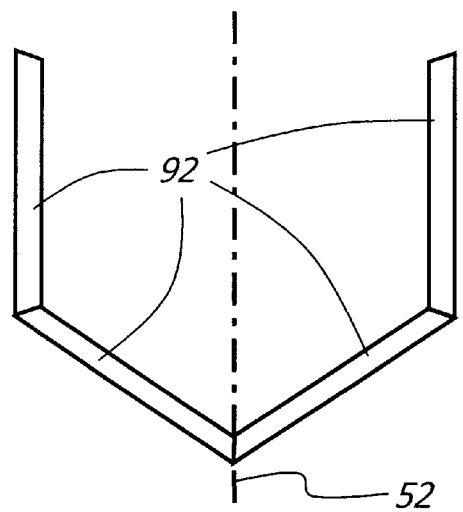
FIGS. 7A, 7B, and 7C are sectional top views of viewing windows according to alternative embodiments of the invention.
Figure 7B:
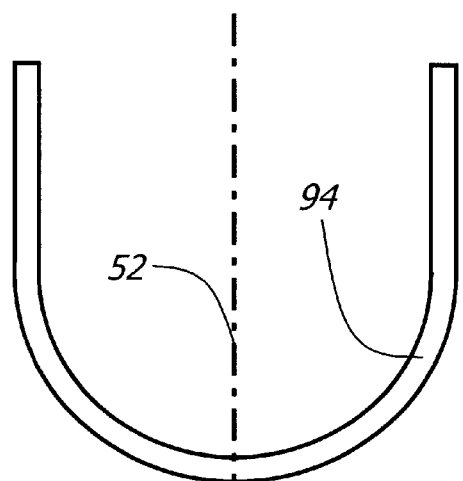
Figure 7C:
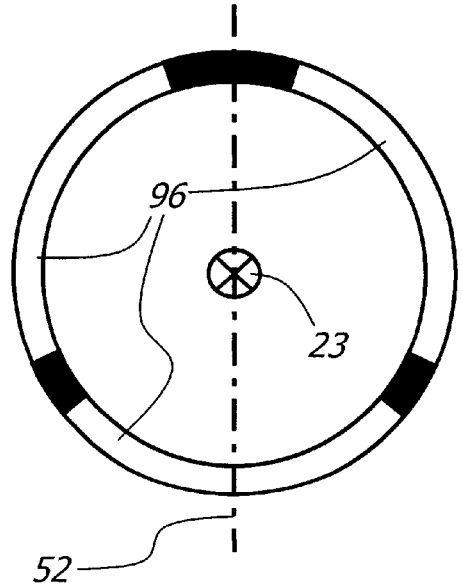

For various reasons, such as ease of manufacture, it may be desirable to replace the spherical viewing window 34 in the preferred embodiment shown in FIGS. 2A, 2B and 2C with an alternative viewing window. A key element of the viewing window is that it is symmetric about the symmetry plane 52. For example, an alternative viewing window that would also afford swing-through-center viewing could be a faceted window comprising one or more flat segments 92 symmetric about the symmetry plane 52, as shown in the top view FIG. 7A. There could be any number of facets combining to form a complete or partial symmetric enclosure sealed to the distal end portion of the endoscope. Alternatively, the viewing window could be a continuous smooth surface 94, as shown in the top view FIG. 7B. Yet another possible viewing window is one that is also radially symmetric about the pivot axis 23, as shown in the top view cross section FIG. 7C. Such a window could be cylindrical, conical, or spherical. It could be continuous or made up of several curved segments 96. It should be appreciated, however, that although the above viewing windows are potential embodiments of the present invention, the spherical viewing window 34, as shown and described, appears to exhibit superior optical characteristics.

Figure 8:
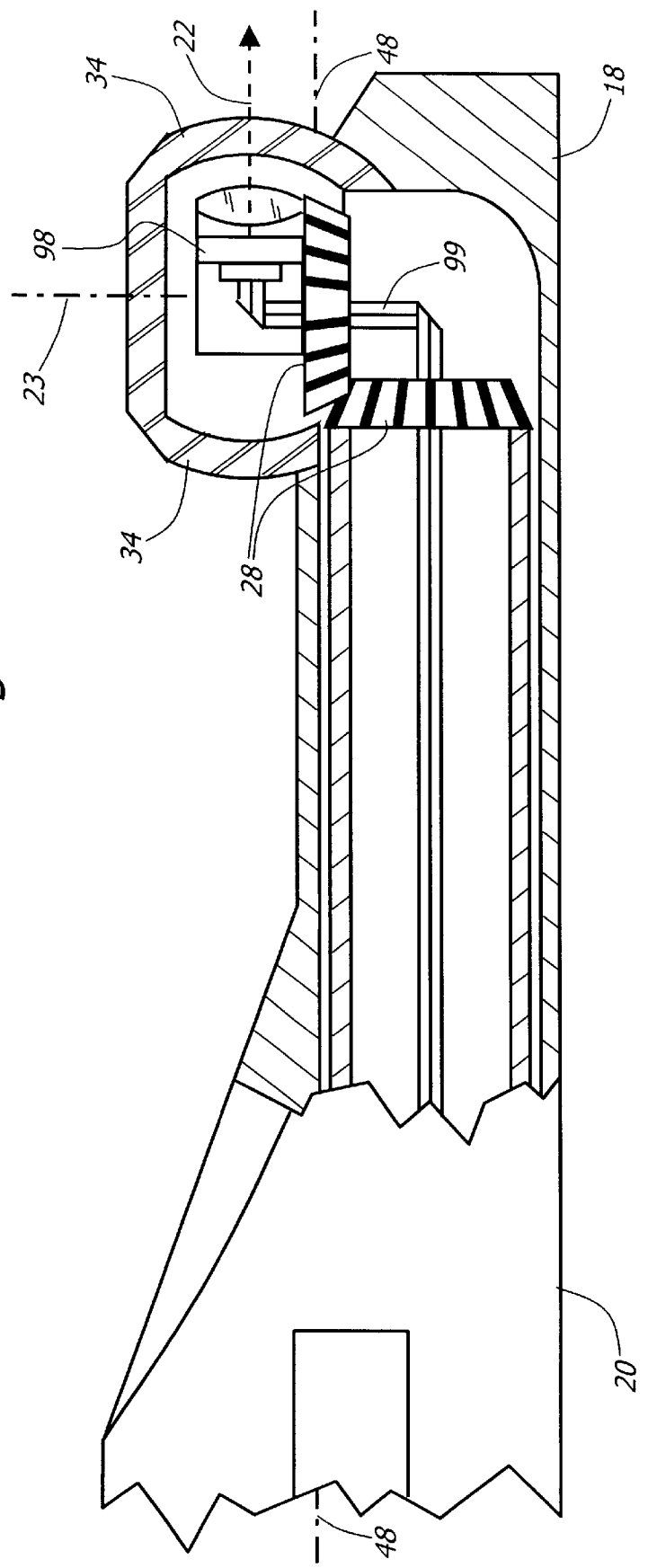
FIG. 8 is a side view of the distal end of an endoscope according to an alternative embodiment of the invention.

FIG. 8 shows a partial section side view of an alternate embodiment of the present invention. This embodiment is very similar to the preferred embodiment shown in FIGS. 2A, 2B, and 2C. It features a rigid metal distal end portion 18 disposed at the distal end of a tubular member 20. A generally spherical viewing window 34 is sealed to the distal end portion 18. Differently in this embodiment, however, a pivotable camera 98 having a view vector 22 is positioned inside the spherical viewing window 34. This embodiment may be operated in a substantially equivalent manner to the preferred embodiment described above. The distal end portion 18 is pivoted about the longitudinal axis 48 by rotating the shaft 20. A pair of metal gears 28 is used to control the rotation of the camera 98 about the pivot axis 23. Total camera rotation may be limited to 180 degrees from forward to limit twist of the camera cable 99, but it will be appreciated by one of skill in the art that conventional slip rings may be used to remove this limitation. Other actuation means such as pull-wires or push-rods may also be acceptable depending on the particular application.

Accordingly, the present invention provides an increased or unlimited scanning range that gives the user increased viewing freedom and backwards viewing capability, a swing-through-center capability by centering the direction of view range on the forward direction, redundant viewing capability such that each particular view can be obtained from two unique viewpoints and three-dimensional viewing. Furthermore, the present invention has secondary advantages, such as redundant viewing window surfaces that give the user an alternative view port should the initial port become blocked by debris. The invention also provides for symmetric left or right-handed use.

The present invention has been described above in terms of a presently preferred embodiment so that an understanding of the present invention can be conveyed. However, there are many configurations for a variable direction-of-view endoscope and method for viewing not specifically described herein but with which the present invention is applicable. Many structural and material variations are possible, as are variations in application. For example, while the examples were given with respect to an endoscope for use in surgical procedures, the present invention would be equally applicable with respect to a borescope for use within various mechanical structures. The scope of the present invention should therefore not be limited by the embodiments illustrated, but rather it should be understood that the present invention has wide applicability with respect to viewing instruments and procedures generally. All modifications, variations, or equivalent elements and implementations that are within the scope of the appended claims should therefore be considered within the scope of the invention.

We claim:

1. An apparatus for use as an endoscope comprising:
   a generally tubular member, a distal end portion, and a proximal end portion, wherein said tubular member has a longitudinal axis;
   a viewing system, comprising a pivotable view vector originating from said distal end portion, wherein said pivotable view vector has a pivot axis that is not parallel to either said pivotable view vector or said longitudinal axis; and
   a viewing window fixedly attached to said distal end portion, wherein said viewing window comprises a transparent viewing area, wherein said transparent viewing area comprises all regions of said viewing window through which said viewing system may view, and wherein the external surface of said transparent viewing area is generally a complete or partial surface of revolution about said pivot axis and substantially bilaterally symmetric about a symmetry plane, wherein said symmetry plane is generally parallel to both said pivot axis and said longitudinal axis near said distal end portion.

2. The apparatus according to claim 1, further comprising a control mechanism that rotates said distal end portion about said longitudinal axis.

3. The apparatus according to claim 1, further comprising a second control mechanism that rotates said pivotable view vector about said pivot axis.

4. The apparatus according to claim 1, wherein said generally tubular member is generally rigid.

5. The apparatus according to claim 1, wherein said generally tubular member is generally flexible.

6. The apparatus according to claim 1, wherein said distal end portion is rigid.

7. The apparatus according to claim 1, wherein the cross-sectional area, perpendicular to said longitudinal axis, of said distal end portion at the proximal extreme of said transparent viewing area is smaller than the cross-sectional area, perpendicular to said longitudinal axis, of said tubular member near said distal end portion.

8. The apparatus according to claim 1, further comprising an illumination system that provides light to a viewed area.

9. The apparatus according to claim 1, wherein said viewing system further comprises a pivotable reflector, wherein said pivotable view vector is adjusted by rotating said pivotable reflector about said pivot axis.

10. The apparatus according to claim 9, further comprising a fixed reflector positioned adjacent to and in communication with said pivorable reflector.

11. The apparatus according to claim 10, further comprising an optical train in communication with said fixed reflector.

12. The apparatus according to claim 10, wherein said pivotable reflector and said fixed reflector are each comprised of a prism.

13. The apparatus according to claim 1, further comprising an imager for capturing images of a viewed area.

14. The apparatus according to claim 1, wherein said external surface of said transparent viewing area also is generally a complete or partial surface of revolution about said view vector, whereby said transparent viewing area is generally spherical and approximately centered about both said pivotable view vector and said pivot axis.

15. The apparatus according to claim 1, wherein said transparent viewing area is comprised of a transparent layer of rigid material.

16. The apparatus according to claim 1, wherein said view vector may be rotated through an unlimited range about said pivot axis.

17. The apparatus according to claim 1, wherein said distal end portion may be rotated through art unlimited range about said longitudinal axis.

18. The apparatus according to claim 1, wherein said pivot axis is generally perpendicular to both said pivotable view vector and said longitudinal axis.

19. The apparatus according to claim 18, wherein said view vector is laterally offset from said longitudinal axis.

20. A process for using the apparatus described in claim 19, wherein said apparatus has an initial configuration comprised of an initial distal end orientation and an initial view vector orientation, comprising the steps of:
rotating said distal end portion about said longitudinal axis from said initial distal end orientation approximately 180 degrees to a final distal end orientation; and
adjusting said view vector to a final view vector orientation symmetric across said symmetry plane from said initial view vector orientation;
whereby the viewing direction of said initial configuration is substantially the same as the viewing direction of a final configuration comprising said final distal end orientation and said final view vector orientation.

21. The process of claim 20, further comprising the steps of:
capturing a first image from said initial configuration;
capturing a second image from said final configuration;
providing both of said first and second images in a stereo image format.

22. An apparatus for use as an endoscope, comprising:
a generally tubular member, a distal end portion, a proximal end portion, wherein said tubular member has a longitudinal axis;
a viewing system, comprising a pivotable view vector originating from said distal end portion, wherein said pivotable view vector has a pivot axis that is not parallel to either said pivotable view vector or said longitudinal axis;
a viewing window fixedly attached to said distal end portion, wherein said viewing window comprises a transparent viewing area wherein said transparent viewing area comprises all regions of said viewing window through which said viewing system may view, and wherein the external surface of said transparent viewing area is generally a complete or partial surface of revolution about said pivot axis and is substantially bilaterally symmetric about a symmetry plane, wherein said symmetry plane is generally parallel to both said pivot axis and said longitudinal axis near said distal end portion;
a means for controllably rotating said distal end portion about said longitudinal axis; and
a means for controllably rotating said pivotable view vector about said pivot axis.

23. A process for using an endoscope comprising a generally tubular member having a distal end portion, a proximal end portion, and a longitudinal axis, and a viewing system, wherein said viewing system comprises a pivotable view vector originating horn said distal end portion, said pivotable view vector having a pivot axis that is generally perpendicular to both said pivotable view vector and said longitudinal axis, wherein said view vector can be rotated to either side of a symmetry plane, said symmetry plane being generally parallel to said longitudinal axis near said distal end portion and generally parallel to said pivot axis, and wherein said endoscope has an initial configuration comprised of an initial distal end orientation and an initial view vector orientation, comprising the steps of:
rotating said distal end portion about said longitudinal axis from said initial distal end orientation approximately 180 degrees to a final distal end orientation; and
adjusting said view vector to a final view vector orientation symmetric across said symmetry plane from said initial view vector orientation;
whereby the viewing direction of said initial configuration is substantially the same as the viewing direction of a final configuration comprising said final distal end orientation and said final view vector orientation.

24. The process of claim 23, wherein said view vector is laterally offset from said longitudinal axis, further comprising;
capturing a first image from said initial configuration;
capturing a second image from said final configuration;
providing both of said first and second images in a stereo image format.

* * * * *